United States Patent [19]

Schmolka

[11] Patent Number: 4,476,107

[45] Date of Patent: Oct. 9, 1984

[54] MOUTHWASH COMPOSITION

[75] Inventor: Irving R. Schmolka, Grosse Ile, Mich.

[73] Assignee: BASF Wyandotte Corporation, Wyandotte, Mich.

[21] Appl. No.: 503,825

[22] Filed: Jun. 13, 1983

[51] Int. Cl.³ .......................... A61K 7/16; A61K 7/18; A61K 7/22

[52] U.S. Cl. ........................................ 424/49; 424/52; 424/54

[58] Field of Search ...................... 426/651; 424/49–58

[56] References Cited

U.S. PATENT DOCUMENTS

| | | | |
|---|---|---|---|
| 2,422,145 | 6/1947 | Taylor | 426/651 |
| 2,435,744 | 2/1948 | Hartman | 426/651 |
| 2,508,978 | 5/1950 | Tribble | 426/651 |
| 2,677,700 | 5/1954 | Jackson | 424/49 |
| 2,773,801 | 12/1956 | Fox | 424/49 |
| 3,639,563 | 2/1972 | Januszewsky | 424/49 |
| 3,666,496 | 5/1972 | Honey et al. | 426/651 |
| 3,674,502 | 7/1972 | Honey et al. | 426/651 |
| 3,947,570 | 3/1976 | Pensak et al. | 424/49 |
| 4,130,638 | 12/1978 | Dhabhar et al. | 424/49 |
| 4,150,151 | 4/1979 | Pader et al. | 424/49 |

*Primary Examiner*—Shep K. Rose
*Attorney, Agent, or Firm*—Bernhard R. Swick

[57] ABSTRACT

Mouthwashes are disclosed which utilize a polyoxyethylene-polyoxybutylene block copolymer wherein the polyoxybutylene portion of the compound has a molecular weight of at least about 500 and the polyoxyethylene portions contribute from about 50 to 90 percent by weight of the compound. Unexpectedly, the nonionic surfactants solubilize flavoring oils at temperatures below 8° C. so that the mouthwash compositions of the invention remain clear and haze free even when stored at low temperatures.

12 Claims, No Drawings

MOUTHWASH COMPOSITION

BACKGROUND OF THE INVENTION

1. Field of the Invention

This invention relates to a good-tasting mouthwash preparation which is stable, visually clear and haze-free at temperatures below 8° C.

2. Description of the Prior Art

Mouthwashes which are widely used to clean the mouth and associated oral areas must have an attractive flavor to obtain consumer acceptance. Such products are essentially solutions of flavoring oils in water containing small amounts of alcohol, glycerol and/or some other sweeteners. The amount of alcohol which can be used to solubilize the flavoring oils is limited. Therefore, it is necessary to devise some other means to solubilize the water insoluble flavoring oils which are a necessary ingredient of such products. There are several requirements for such solubilizing agents. They must obviously be tasteless, or, at most, exhibit a bland innocuous taste. Also, they should be capable of maintaining the clarity of the mouthwash at a low use level, down to very low temperatures, i.e., below 8° C., such as 5° C., since mouthwashes are usually stored in a cool location.

Currently, many commercial mouthwashes incorporate an ethylene oxide adduct of a mixture of oleate esters of sorbitol and sorbitol anhydrides. Although this is an execellent solubilizing agent, it has a very bitter taste. Usually it is used in conjunction with other nonionic surfactants, to maintain the clarity of the mouthwash at low temperatures. Another disadvantage of the use of this solubilizing agent and other ethoxylated esters and fatty alcohols is their property of inactivating germicidal or anti-caries agents which are sometimes used in liquid oral products which are not designed for ingestion While there are many surfactants on the market which serve as solubilizers for flavoring oils and which are effective at room temperature, they are not effective at very low temperatures such as around 5° C. or, in other words, temperatures below 8° C. As previously pointed out, this is an important factor since mouth rinses are usually stored in a cool location.

Copending U.S. patent application, Ser. No. 466,733 discloses an oral product with good taste which has improved clarity at ambient temperatures utilizing a polyoxyethylene derivative of a fatty alcohol containing about 15 to 20 carbon atoms.

| Issued Patents of Interest | | |
| --- | --- | --- |
| Patent No. | Issued | Inventor(s) |
| 4,323,552 | 4/6/82 | Schmolka |
| 3,639,563 | 2/1/72 | Januszewski |
| 3,947,570 | 3/30/76 | Pensak et al |
| 2,677,700 | 5/4/54 | Jackson et al |
| 4,150,151 | 4/17/79 | Pader et al |
| 3,674,502 | 7/4/72 | Honey et al |
| 4,132,770 | 1/2/79 | Barth |

SUMMARY OF THE INVENTION

A flavored mouthwash can be prepared having good taste characteristics and improved clarity at temperatures below 8° C. by utilizing a particular nonionic surfactant solubilizing agent. The nonionic surfactant selected for use in the mouthwash composition of the instant invention is a polyoxyethylene-polyoxybutylene copolymer wherein the polyoxybutylene portion of the compound has a molecular weight of at least 500 and the polyoxyethylene portions contribute from about 50 to 90 percent by weight of the compound.

DETAILED DESCRIPTION OF THE INVENTION

While it is known to use nonionic surfactants to solubilize flavoring agents in the prior art including polyoxyethylene-polyoxypropylene copolymers, such nonionic surfactants are generally successful solubilizers only at ambient temperatures or above. Accordingly, it was totally unexpected to find that block polymers of butylene oxide and ethylene oxide, as described above, have the property to solubilize insoluble flavoring oils and to maintain the clarity of these solutions, when diluted with a minimum of alcohol in water, when cooled to less than 8° C. This is an important property since such mouthwashes are often stored at low temperatures to prevent deterioration. The block copolymers of the invention are members of a family comprised of an almost unlimited number of nonionic surfactants in a series of block copolymers that consists of water-soluble poly(oxyethylene) groups at both ends of a water-insoluble poly(oxybutylene) chain.

The first step in making the surfactants employed in the present invention is the controlled addition of butylene oxide at the hydroxyl groups of a low molecular weight water-soluble polyol initiator. Suitable initiators include glycerine, trimethylolpropane, pentaerythritol, ethylene glycol, propylene glycol and preferably butylene glycol and most preferably 1,4-butylene glycol. It is also preferred to employ 1,2-butylene oxide for the addition to the two hydroxyl groups of the 1,4-butylene glycol nucleus. At a molecular weight of about 500, the resulting polyoxybutylene glycol becomes water-insoluble which serves as a hydrophobe which is then tailored to the desired molecular weight, i.e., greater than 500 and preferably between 1000 and 5000. Ethylene oxide is added to sandwich the hydrophobic base between hydrophilic poly(oxyethylene) groups which are controlled in length. The surfactants employed in the present invention are members of the group in which the ethylene oxide addition is controlled to constitute from 50 to 90 percent by weight of the final molecule.

The hydrophobic oxybutylene chains may optionally, but advantageously, contain small amounts of ethylene oxide and/or propylene oxide which may partially replace the butylene oxide to provide a ratio in the predominantly oxybutylene hydrophobic chains of ethylene oxide and/or propylene oxide groups to butylene oxide groups of from about 1:20 to about 1:3. Similarly, the oxyethylene hydrophilic chains may also optionally, but advantageously, contain small amounts of alkylene oxides such as propylene oxide and butylene oxide which may partially replace the ethylene oxide units whereby the ratio of propylene oxide and/or butylene oxide to ethylene oxide in the hydrophilic chains may range from 1:20 to 1:4, preferably 1:20 to 1:9.

It is to be understood that the expression polyoxyethylene-polyoxybutylene block copolymer includes such amounts of propylene oxide and/or ethylene oxide groups in the hydrophobic polyoxybutylene chains and such amounts of propylene oxide and/or butylene oxide groups with the hydrophilic polyoxyethylene chains.

The preferred polyoxybutylene-polyoxyethylene block copolymers have the general formula:

$$HO(C_2H_4O)_a(C_4H_8O)_b(C_2H_4O)_cH$$

wherein a+c equals 50 to 90 percent of the total weight of the copolymer and b represents a molecular weight of the polyoxybutylene portion of the polymer molecule which is greater than 500 and preferably between 1000 and 5000.

A more detailed disclosure of the preparation of the surfactants can be found, for instance, in U.S. Pat. No. 2,828,345, hereby incorporated by reference.

Generally, the nonionic surfactant according to this invention is utilized in the mouthwash as the sole surfactant component of the composition but it is also useful when blended with other conventional prior art surfactants in a major proportion of the mixture. Generally, the nonionic surfactant of the invention is about 0.5 to 5.0 percent, preferably about 2.0 to 4.0 percent, and most preferably, about 2.5 to 3.5 percent, by weight of the mouthwash composition of the invention.

Minor amounts of prior art surfactants can be employed in admixture with the nonionic surfactant of the invention without substantially contributing to reduction in clarity of the composition. Where mixtures of surfactants are used, generally about 2 to 20 percent by weight of conventional prior art surfactants based on total weight of surfactants is used with the surfactants of the invention.

Conventional surfactants suitable for use in admixture with the polyoxyethylene-polyoxybutylene nonionic surfactant of the invention include nonionic surfactants such as condensates of ethylene oxide with polymers of propylene oxide and amphoteric agents such as quarternized imidazole derivatives. Additional examples of conventional nonionic surfactants suitable for use in minor amounts in the oral compositions of the invention are condensates of an alpha-olefin epoxide and a polyhydric alcohol containing 2 to about 10 carbon atoms and 2 to 6 hydroxyl groups with either ethylene oxide or a water-soluble heteric mixture of ethylene oxide and propylene oxide. Such heteric polymers have a molecular weight in the range of 400 to 1600 and contain 40 to 80 percent by weight of the ethylene oxide or water-soluble mixture of ethylene oxide and propylene oxide. The ratio of alpha-olefin epoxide to polyhydric alcohol is in a molar ratio of 1:1 to 1:3.

In addition, anionic or cationic organic surfactants can be employed in admixture with the nonionic surfactants of the invention. Suitable anionic and cationic surfactants are water-soluble salts of higher fatty acids, monoglycerides of hydrogenated coconut oil fatty acids, higher alkyl sulfates such as sodium lauryl sulfate, alkylaryl sulfonates, such as sodium dodecylbenzene sulfonate, higher alkyl sulfoacetates, higher fatty acid esters of 1,2-dihydroxypropane sulfonates, olefin sulfonates and the substantially saturated higher aliphatic acrylamides of lower aliphatic amino carboxylic compounds such as those having 12 to 16 carbon atoms in the fatty acid or acyl radicals and the like. Examples of useful substantially-saturated higher aliphatic acylamides of lower aliphatic amino carboxylic acids are N-lauroyl sarcosine and the sodium, potassium and ethanolamine salts of N-lauroyl, N-myristoyl, or N-palmitoyl sarcosine. These should be substantially free from soap or similar higher fatty acid materials which tend to substantially reduce the effectiveness of these compounds.

Generally, the flavoring component is present as a denaturant in the non-toxic alcohol component, i.e., ethyl alcohol, utilized in a mouthwash composition. The conventional flavoring components are exemplified by the following materials: menthol, anise oil, benzaldehyde, bitter almond oil, camphor, cedar leaf oil, chlorothymol, cinnamic aldehyde, cinnamon oil, citronella oil, clove oil, eucalyptol, lavendar oil, menthol, mustard oil, peppermint oil, methyl salicylate, phenyl salicylate, pine oil, pine needle oil, rosemary oil, sassafras oil, spearmint oil, thyme oil, thymol, and wintergreen oil.

The water-insoluble flavoring oils utilized in the oral compositions of the invention, for instance peppermint oil, require a water solubilizing amount of the nonionic surfactant of the invention in order to effectually render the oral composition visually clear at temperatures below 8° C. Generally, where peppermint oil is employed in the composition, the weight ratio of said nonionic surfactant to said peppermint oil is greater than 1:1. Preferably, the ratio of said surfactant to peppermint oil is about 10:1 to 100:1 and most preferably, 30:1 to 50:1.

The mouthwash compositions of the invention generally contain about 60 to 90 percent, preferably about 70 to 80 percent by weight of water and from 0 to about 20, preferably about 5 to 10 percent by weight of a nontoxic alcohol such as isopropanol or ethanol.

In addition to the flavoring component and the nonionic surfactant which is utilized as a solubilizing agent, the mouthwash compositions of the invention generally contain optional effective amounts of antibacterial and antiplaque agents such as quaternary ammonium compounds or the substantially saturated aliphatic acyl amides. Generally, these antibacterial antiplaque agents are utilized in amounts of about 0.1 to about 0.3 percent by weight of the mouthwash composition. Among the most common of these antibacterial antiplaque compounds is benzethonium chloride, also known as Hyamine 1622 or di-isobutyl phenoxyethoxyethyl dimethyl benzyl ammonium chloride. In an oral preparation this material is highly effective in promoting oral hygiene by reducing formation of dental plaque and calculus. Reduction of plaque and calculus is generally accompanied by reduction in caries formation. Other cationic antibacterial agents of this type are those mentioned, for instance, in U.S. Pat. Nos. 2,984,639; 3,325,402; 3,703,583; and 3,431,208 and British Pat. No. 1,319,396.

Other antibacterial antiplaque compounds include those in which one or two of the substituents on the quaternary nitrogen has a carbon chain length (typically alkyl group) of some 8 to 20, typically 10 to 18, carbon atoms while the remaining substituents have a lower number of carbon atoms (typically alkyl or benzyl group), such as 1 to 7 carbon atoms, typically methyl or ethyl groups. Dodecyl trimethyl ammonium bromide, benzyl dimethyl stearyl ammonium chloride, cetyl pyridinium chloride and quaternized 5amino-1,3-bis (2-ethylhexyl)-5-methyl hexa hydro-pyrimidine are typical quaternary ammonium antibacterial agents.

Other types of cationic antibacterial agents which are desirably incorporated in oral compositions to promote oral hygiene by reducing plaque formation are the amidines such as the substituted guanidines, e.g., chlorhexidine and the corresponding compound, alexidine, having 2-ethylhexyl groups instead of chlorophenyl groups.

Additional adjuvants can be added to provide color, flavor, or sweetening effects, as desired. Examples of suitable colors are F, D and C Blue #1, Red #4, Green #3, Yellow #5 and Red #40, D and C Red #3, Red #19 and Red #40. Suitable sweetening agents include sucrose, lactose, maltose, sorbitol, sodium cyclamate, glycerine, propylene glycol, and sodium saccharine. Citric acid is often utilized as a flavor additive. The coloring agent or agents are typically added in an amount of about 0.0005 to 0.01 percent and the flavor and sweetening agents together, referred to herein as "flavoring material," are added in amount of about 0.01 to 15.0 percent all by weight of the mouthwash composition. Some compositions do not include a sweetening agent and accordingly in such compositions the "flavoring material" is all flavoring agent. The preferred amounts are about 8 percent to about 12.0 percent by weight of the mouthwash composition. Other conventional additives may be employed in an amount up to about 10 percent by weight.

In certain forms of this invention a fluoride-providing compound is present in the oral preparation. These compounds may be slightly soluble in water or may be fully water-soluble. They are characterized by their ability to release fluoride ions in water and by substantial freedom from reaction with other compounds of the oral preparation. Among these materials are inorganic fluoride salts, such as soluble alkali metal, alkaline earth metal and heavy metal salts, for example, sodium fluoride, potassium fluoride, ammonium fluoride, lead fluoride, a copper fluoride such as cuprous fluoride, zinc fluoride, a tin fluoride such as stannic fluoride or stannous chlorofluoride, barium fluoride, sodium fluorosilicate, ammonium fluorosilicate, sodium fluorozirconate, sodium monofluorophosphate, aluminum mono- and difluorophosphate. Alkali metal and tin fluorides, such as sodium and stannous fluorides, sodium monofluorophosphate and mixtures thereof, are preferred. A mixture of sodium fluoride and sodium monofluorophosphate is particularly desirable.

The amount of the fluoride-providing compound is dependent to some extent upon the type of compound and its solubility, but it must be a non-toxic amount. Any suitable minimum amount of such compound may be used, but it is preferable to employ sufficient compound to release up to 0.13 percent, preferably from 0.0013 percent to 0.1 percent and most preferably from 0.0013 percent to 0.05 percent, by weight, of fluoride ion.

Generally, a buffering ingredient is also added to the mouthwash compositions of the invention in order to prevent natural degradation of the flavoring components of the mouthwash. Generally, the pH of the mouthwash is adjusted to about 5 to 10, preferably from about 6 to 8. The buffering ingredient such as an alkali metal salt of a weak organic acid, for instance, sodium benzoate, sodium citrate, sodium phosphate, or potassium tartrate is generally added in an amount of about 0.1 to about 1.0 percent by weight.

The mouthwash compositions of the invention are prepared using methods similar to those well known in the art. Typically, the ingredients are combined in a specified amount in an amount of water sufficient to bring the total of components to 100 percent by weight. Preferably, the alcohol-soluble components are separately premixed in a suitable mixing vessel and subsequently added to the water. Those components having solubility in water are preferably added to the water before mixing the alcohol premixture into the water.

The following examples more fully describe the mouthwash of the invention and show the unexpected results obtained by the use of the nonionic surfactants disclosed herein. Unless otherwise indicated, all parts, percentages and proportions are by weight and all temperatures are in degrees centigrade.

EXAMPLE 1

A mouthwash of the invention was prepared by adding 1.0 part of the surfactant of the invention and 0.75 part of peppermint oil to 98.4 parts of a blend of water, ethyl alcohol, F, D and C Blue #1 and Yellow #5 dyes and sodium saccharin. The mixture was bottled and the appearance noted. The solution which was clear at ambient temperature was placed in a cooling bath and observed periodically. The solution remained clear even when cooled to a temperature as low as 8° C. The composition of the mouthwash was as follows:

| Ingredient | Parts by Weight |
| --- | --- |
| Water | 83.29 |
| 95% ethyl alcohol (aqueous) | 15.00 |
| FD&C Blue #1 (0.1% ethyl alcohol solution) | 0.01 |
| FD&C Yellow #5 (1.0% ethyl alcohol solution) | 0.01 |
| Sodium saccharin | 0.10 |
| Polyoxyethylene adduct of a polyoxybutylene hydrophobic base having a molecular weight of about 3000 wherein the oxyethylene content is about 80 weight percent of the molecule | 1.00 |
| Peppermint Oil | 0.75 |

EXAMPLE 2

Example 1 was repeated with the exception that the nonionic surfactant was replaced with the polyoxyethylene adduct of a polyoxybutylene hydrophobic base having a molecular weight of about 3000 and wherein the oxyethylene content is about 70 weight percent of the molecule. The solution which was clear at ambient temperature was placed in a cooling bath and observed periodically. The solution remained clear even when cooled to 8° C.

EXAMPLE 3

Example 1 was repeated with the exception that the nonionic surfactant was replaced with the polyoxyethylene adduct of a polyoxybutylene hydrophobic base having a molecular weight of about 2400 and wherein the oxyethylene content is about 80 weight percent of the molecule. The solution which was clear at ambient temperature was placed in a cooling bath and observed periodically. The solution remained clear even when cooled to 8° C.

EXAMPLE 4

(Comparative Example)

Example 1 was repeated with the exception that the nonionic surfactant was replaced with the polyoxyethylene adduct of a polyoxypropylene hydrophobic base having a molecular weight of about 4000 and wherein the oxyethylene content is about 70 weight percent of the molecule. This solution which was clear at ambient temperature was placed in a cooling bath and observed periodically. The solution had become cloudy at 8° C.

EXAMPLES 5-9

These examples further illustrate the superior solubilizing effect on flavors by the use of the nonionics of this invention as compared to prior art nonionics.

A mixture of 1 part by weight of methyl salicylate and 9 parts of the surfactant was added to a beaker containing 100 ml water. The mixture was allowed to come to equilibrium at ambient (25° C.) temperature and then cooled to 5° C. Observations were made as to clarity and turbidity which are shown below in Table II.

TABLE II

| | Clarity | |
|---|---|---|
| Nonionic | Ambient Temperature | 5° C. |
| Nonionic No. 1 | Cloudy | Cloudy |
| Nonionic No. 2 | Cloudy | Cloudy |
| Nonionic No. 3 | Cloudy | Cloudy |
| Nonionic No. 4 | Clear | Cloudy |
| Nonionic No. 5 | Clear | Clear |

Nonionic No. 1 is a polyethylene glycol sorbitan isostearate polymer containing 20 moles of oxyethylene groups.

Nonionic No. 2 is a polyoxyethylene adduct of a polyoxypropylene hydrophobic base having a molecular weight of about 1750 wherein the oxyethylene content is about 80 weight percent of the molecule.

Nonionic No. 3 is the polyoxyethylene adduct of a polyoxypropylene hydrophobic base having a molecular weight of about 3250 wherein the oxyethylene content is about 80 weight percent of the molecule.

Nonionic No. 4 defines the polyoxyethylene adduct of a polyoxypropylene hydrophobic base having a molecular weight of about 4000 wherein the oxyethylene content is about 70 weight percent of the molecule.

Nonionic No. 5 defines the polyoxyethylene adduct of a polyoxybutylene hydrophobic base having a molecular weight of about 3000 wherein the oxyethylene content is about 80 weight percent of the molecule.

Nonionic No. 5 was the only nonionic within the scope of the instant invention and was the only one that was clear even at a temperature of 5° C.

The embodiments of the invention in which an exclusive privilege or property is claimed are defined as follows:

1. A pleasant tasting aqueous mouthwash which is stable, visually clear, and haze free at temperatures below 8° C. comprising about 60 to 90 percent by weight of water, about 0.01 to 15 percent by weight of flavoring material, from 0 to about 20 percent by weight of a non-toxic alcohol and about 0.5 to 5.0 percent by weight of a nonionic surfactant consisting essentially of a polyoxyethylene-polyoxybutylene block copolymer wherein the polyoxybutylene portion of the compound has a molecular weight of at least about 500 and the polyoxyethylene portions contribute from about 50 to 90 percent by weight of the compound.

2. The composition of claim 1 wherein said polyoxyethylene-polyoxybutylene block copolymer has the formula:

$$HO(C_2H_4O)_a(C_4H_8O)_b(C_2H_4O)_cH$$

wherein a, b and c are integers such that the copolymer consists of 50 to 90 percent by weight polyoxyethylene groups and wherein the molecular weight of the polyoxybutylene groups is at least about 500.

3. The composition of claim 2 wherein the molecular weight of the polyoxybutylene groups is about 1000 to 5000.

4. A mouthwash according to claim 3 further including an additional nonionic surfactant.

5. A mouthwash according to claim 4 further including an additional surfactant selected from the group consisting of anionic and cationic surfactants.

6. A mouthwash according to claim 3 wherein said non-toxic alcohol is ethanol or isopropanol which is present in an amount of from about 5.0 to 10.0 percent by weight.

7. The mouthwash of claim 1 including a coloring agent in an amount of about 0.0005 to 0.01 percent by weight.

8. The composition of claim 7 wherein said composition includes additional conventional additives in total amount up to about 10 percent by weight.

9. The composition of claim 8 wherein said additional conventional additives are selected from perfumes, buffering agents, preservatives and mixtures thereof.

10. A mouthwash according to claim 9 further including an additional nonionic surfactant.

11. A mouthwash according to claim 10 further including an additional surfactant selected from the group consisting of anionic and cationic surfactants.

12. A mouthwash according to claim 6 wherein said flavoring material is peppermint oil and the weight ratio of nonionic surfactant to peppermint oil is about 1:1 to 100:1.

* * * * *